US009532801B2

(12) United States Patent
Davis

(10) Patent No.: US 9,532,801 B2
(45) Date of Patent: Jan. 3, 2017

(54) SEAL ANCHOR FOR USE IN SURGICAL PROCEDURES

(71) Applicant: Covidien LP, Mansfield, MA (US)

(72) Inventor: Michael Davis, Austin, TX (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/486,204

(22) Filed: Sep. 15, 2014

(65) Prior Publication Data

US 2015/0005583 A1 Jan. 1, 2015

Related U.S. Application Data

(63) Continuation of application No. 13/223,336, filed on Sep. 1, 2011, now Pat. No. 8,864,659.

(Continued)

(51) Int. Cl.
*A61B 1/32* (2006.01)
*A61B 17/34* (2006.01)

(52) U.S. Cl.
CPC .... *A61B 17/3423* (2013.01); *A61B 2017/3429* (2013.01); *A61B 2017/3443* (2013.01)

(58) Field of Classification Search
CPC .. A61B 17/02; A61B 17/0218; A61B 17/0293
(Continued)

(56) References Cited

U.S. PATENT DOCUMENTS 4,402,683 A 9/1983 Kopman
5,242,415 A 9/1993 Kantrowitz et al.
(Continued)

FOREIGN PATENT DOCUMENTS

DE 19735875 A1 3/1999
EP 0950376 A1 10/1999
(Continued)

OTHER PUBLICATIONS

European Search Report dated Jan. 1, 2014 from corresponding EP Application No. EP11250800.7. (9 pgs.).
(Continued)

*Primary Examiner* — Anu Ramana
*Assistant Examiner* — Jessica Weiss

(57) ABSTRACT

A surgical apparatus for positioning within a tissue tract accessing an underlying body cavity, includes a seal anchor member comprising a compressible material and being adapted to transition between a first expanded condition to facilitate securing of the seal anchor member within the tissue tract and in substantial sealed relation with tissue surfaces defining the tissue tract and a second compressed condition to facilitate at least partial insertion of the seal anchor member within the tissue tract. The seal anchor member defines a central longitudinal axis and has leading and trailing ends. At least one longitudinal object port extends between the leading and trailing ends and is adapted for reception of a surgical object whereby compressible material defining the at least one longitudinal object port is adapted to deform to establish a substantial sealed relation with the object. The seal anchor member includes at least two separable anchor segments dimensioned to be positioned in adjacent stacked relation to selectively alter the longitudinal length of the seal anchor member to accommodate tissue tracts of different lengths.

16 Claims, 5 Drawing Sheets

Related U.S. Application Data

(60) Provisional application No. 61/416,511, filed on Nov. 23, 2010.

(58) Field of Classification Search
USPC ............ 600/201–246; 606/213; 604/96.01, 604/104–109, 164.01, 167
See application file for complete search history.

(56) References Cited

U.S. PATENT DOCUMENTS

| | | | |
|---|---|---|---|
| 5,672,168 | A | 9/1997 | de la Torre et al. |
| 6,171,282 | B1 | 1/2001 | Ragsdale |
| 6,578,577 | B2 | 6/2003 | Bonadio et al. |
| 6,589,167 | B1 | 7/2003 | Shimomura et al. |
| 6,676,639 | B1 | 1/2004 | Ternstrom |
| 6,811,546 | B1 | 11/2004 | Callas et al. |
| 6,840,951 | B2 | 1/2005 | de la Torre et al. |
| 6,939,296 | B2 | 9/2005 | Ewers et al. |
| 7,153,261 | B2 | 12/2006 | Wenchell |
| 7,217,277 | B2 | 5/2007 | Parihar et al. |
| 7,244,244 | B2 | 7/2007 | Racenet et al. |
| 7,276,075 | B1 | 10/2007 | Callas et al. |
| 7,294,103 | B2 | 11/2007 | Bertolero et al. |
| 7,300,399 | B2 | 11/2007 | Bonadio et al. |
| 7,331,940 | B2 | 2/2008 | Sommerich |
| 7,344,547 | B2 | 3/2008 | Piskun |
| 7,377,898 | B2 * | 5/2008 | Ewers et al. ............ 600/208 |
| 7,393,322 | B2 | 7/2008 | Wenchell |
| 7,445,597 | B2 | 11/2008 | Butler et al. |
| 7,473,221 | B2 | 1/2009 | Ewers et al. |
| 7,481,765 | B2 | 1/2009 | Ewers et al. |
| 7,537,564 | B2 | 5/2009 | Bonadio et al. |
| 7,540,839 | B2 | 6/2009 | Butler et al. |
| 7,559,893 | B2 | 7/2009 | Bonadio et al. |
| 7,650,887 | B2 | 1/2010 | Nguyen et al. |
| 7,704,207 | B2 | 4/2010 | Albrecht et al. |
| 7,717,847 | B2 | 5/2010 | Smith |
| 7,727,146 | B2 | 6/2010 | Albrecht et al. |
| 7,736,306 | B2 | 6/2010 | Brustad et al. |
| 7,766,824 | B2 | 8/2010 | Jensen et al. |
| 7,811,251 | B2 | 10/2010 | Wenchell et al. |
| 7,815,567 | B2 | 10/2010 | Albrecht et al. |
| 7,909,760 | B2 | 3/2011 | Albrecht et al. |
| 8,864,659 | B2 | 10/2014 | Davis |
| 2003/0014076 | A1 | 1/2003 | Mollenauer et al. |
| 2005/0096695 | A1 | 5/2005 | Olich |
| 2005/0107663 | A1 | 5/2005 | Saadat et al. |
| 2006/0071432 | A1 | 4/2006 | Staudner |
| 2006/0200185 | A1 | 9/2006 | Marchek et al. |
| 2006/0200186 | A1 | 9/2006 | Marchek et al. |
| 2006/0224120 | A1 | 10/2006 | Smith et al. |
| 2006/0247499 | A1 | 11/2006 | Butler et al. |
| 2006/0247516 | A1 | 11/2006 | Hess et al. |
| 2006/0247673 | A1 | 11/2006 | Voegele et al. |
| 2006/0247678 | A1 | 11/2006 | Weisenburgh et al. |
| 2007/0060884 | A1 | 3/2007 | Hayek |
| 2007/0208312 | A1 | 9/2007 | Norton et al. |
| 2007/0270654 | A1 | 11/2007 | Pignato et al. |
| 2007/0270882 | A1 | 11/2007 | Hjelle et al. |
| 2008/0091143 | A1 | 4/2008 | Taylor et al. |
| 2008/0161826 | A1 | 7/2008 | Guiraudon |
| 2009/0012477 | A1 | 1/2009 | Norton et al. |
| 2009/0093752 | A1 | 4/2009 | Richard et al. |
| 2009/0093850 | A1 | 4/2009 | Richard |
| 2009/0187079 | A1 | 7/2009 | Albrecht et al. |
| 2009/0221968 | A1 | 9/2009 | Morrison et al. |
| 2009/0326330 | A1 | 12/2009 | Bonadio et al. |
| 2009/0326332 | A1 | 12/2009 | Carter |
| 2010/0100043 | A1 | 4/2010 | Racenet |
| 2010/0261975 | A1 * | 10/2010 | Huey et al. ............ 600/208 |
| 2010/0280326 | A1 | 11/2010 | Hess et al. |
| 2011/0028891 | A1 | 2/2011 | Okoniewski |
| 2011/0034778 | A1 | 2/2011 | Kleyman |
| 2011/0082341 | A1 | 4/2011 | Kleyman et al. |
| 2011/0082343 | A1 | 4/2011 | Okoniewski |
| 2011/0082346 | A1 | 4/2011 | Stopek |
| 2011/0118553 | A1 | 5/2011 | Stopek |
| 2011/0124969 | A1 | 5/2011 | Stopek |
| 2011/0124970 | A1 | 5/2011 | Kleyman |
| 2011/0125186 | A1 | 5/2011 | Fowler et al. |
| 2011/0144449 | A1 * | 6/2011 | Ortiz et al. ............ 600/216 |
| 2011/0166423 | A1 | 7/2011 | Farascioni et al. |

FOREIGN PATENT DOCUMENTS

| | | |
|---|---|---|
| EP | 1312318 A1 | 5/2003 |
| EP | 1774918 A1 | 4/2007 |
| WO | 97/42889 | 11/1997 |
| WO | 01/08581 | 2/2001 |
| WO | 03/034908 A2 | 5/2003 |
| WO | 2004/043275 | 5/2004 |
| WO | 2004/054456 | 7/2004 |
| WO | 2004/075741 | 9/2004 |
| WO | 2004/075930 | 9/2004 |
| WO | 2006/019723 | 2/2006 |
| WO | 2006/100658 A2 | 9/2006 |
| WO | 2006/110733 | 10/2006 |
| WO | 2008/015566 A2 | 2/2008 |
| WO | 2008/042005 | 4/2008 |
| WO | 2008/103151 | 8/2008 |
| WO | 2008/121294 A1 | 10/2008 |
| WO | 2009/036343 | 3/2009 |
| WO | 2009/046164 A1 | 4/2009 |

OTHER PUBLICATIONS

Japanese Office Action for Japanese Patent Appln. No. 2011-200623 mailed Apr. 20, 2015.

* cited by examiner

SEAL ANCHOR FOR USE IN SURGICAL PROCEDURES

CROSS-REFERENCE TO RELATED APPLICATIONS

This application is a continuation of U.S. patent application Ser. No. 13/223,336 filed Sep. 1, 2011, now U.S. Pat. No. 8,864,659, which claims benefit of U.S. Provisional Application No. 61/416,511 filed Nov. 23, 2010, and the disclosures of each of the above-identified applications are hereby incorporated by reference in their entirety.

BACKGROUND

1. Technical Field

The present disclosure relates to a seal for use in a surgical procedure. More particularly, the present disclosure relates to a seal anchor apparatus adapted for insertion into an incision in tissue, and, for the sealed reception of one or more surgical objects such that a substantially fluid-tight seal is formed with both the tissue and the surgical object, or objects.

2. Background of the Related Art

Today, many surgical procedures are performed through small incisions in the skin, as compared to the larger incisions typically required in traditional procedures, in an effort to reduce both trauma to the patient and recovery time. Generally, such procedures are referred to as "endoscopic", and when performed on the patient's abdomen, is referred to as "laparoscopic". Throughout the present disclosure, the term "minimally invasive" should be understood to encompass both endoscopic and laparoscopic procedures.

During a typical minimally invasive procedure, surgical objects, such as surgical access devices, e.g., trocar and cannula assemblies, or endoscopes, are inserted into the patient's body through the incision in tissue. In general, prior to the introduction of the surgical object into the patient's body, insufflation gasses are used to enlarge the area surrounding the target surgical site to create a larger, more accessible work area. Accordingly, the maintenance of a substantially fluid-tight seal is desirable so as to prevent the escape of the insufflation gases and the deflation or collapse of the enlarged surgical site.

To this end, various valves and seals are used during the course of minimally invasive procedures and are widely known in the art. However, a continuing need exists for an apparatus that can be inserted directly into the incision in tissue and that can accommodate tissue tracts of varying lengths and a variety of surgical objects while maintaining the integrity of an insufflated workspace.

SUMMARY

A surgical apparatus for positioning within a tissue tract accessing an underlying body cavity, includes a seal anchor member comprising a compressible material and being adapted to transition between a first expanded condition to facilitate securing of the seal anchor member within the tissue tract and in substantial sealed relation with tissue surfaces defining the tissue tract and a second compressed condition to facilitate at least partial insertion of the seal anchor member within the tissue tract. The seal anchor member defines a central longitudinal axis and has leading and trailing ends. At least one longitudinal object port extends between the leading and trailing ends and is adapted for reception of a surgical object whereby compressible material defining the at least one longitudinal object port is adapted to deform to establish a substantial sealed relation with the object. The seal anchor member includes at least two separable anchor segments dimensioned to be positioned in adjacent stacked relation to selectively alter the longitudinal length of the seal anchor member to accommodate tissue tracts of different lengths. Each anchor segment defines longitudinal object port segments adapted to be aligned when in the adjacent stacked relation to define the at least one longitudinal object port of the seal anchor member. The seal anchor member may include at least three anchor segments with each of the anchor segments defining the longitudinal object port segments. Means for securing the anchor segments in juxtaposed stacked relation may be provided.

The seal anchor member may include a supplemental longitudinal opening. An elongate securing member may be positionable within the secondary longitudinal opening of the seal anchor member. The securing member is dimensioned and adapted to retain the at least three anchor segments in the adjacent stacked relation. The at least three anchor segments may include supplemental opening segments in communication with each other when the at least three anchor segments are in the adjacent stacked relation. The supplemental opening segments define the supplemental longitudinal opening of the seal anchor member to receive the securing member. Each of the at least three anchor segments include first and second supplemental opening segments in communication with each other when the at least three anchor segments are in the adjacent stacked relation. The first and second supplemental opening segments define first and second longitudinal openings of the seal anchor member to receive the securing member.

First and second securing members may be positionable within the first and second supplemental longitudinal openings respectively to retain the at least three anchor segments in the adjacent stacked relation. The securing member may include a flexible filament, or, in the alternative, may be a substantially rigid element.

The at least three anchor segments may include a leading anchor segment, a trailing anchor segment and an intermediate anchor segment. At least one of the leading and the trailing anchor segments having a flange portion to facilitate retention of the seal anchor member relative to the tissue tract. Each of the leading and the trailing anchor segments may include a flange portion to facilitate retention of the seal anchor relative to the tissue tract.

The at least one longitudinal object port may be in general longitudinal alignment with the central longitudinal axis of the seal anchor member. A plurality of longitudinal object ports may be provided.

The seal anchor member may comprise one of a foam material or a gel material.

BRIEF DESCRIPTION OF THE DRAWINGS

Various embodiments of the present disclosure are described hereinbelow with references to the drawings, wherein.

DETAILED DESCRIPTION OF THE EMBODIMENTS

Figure 1:
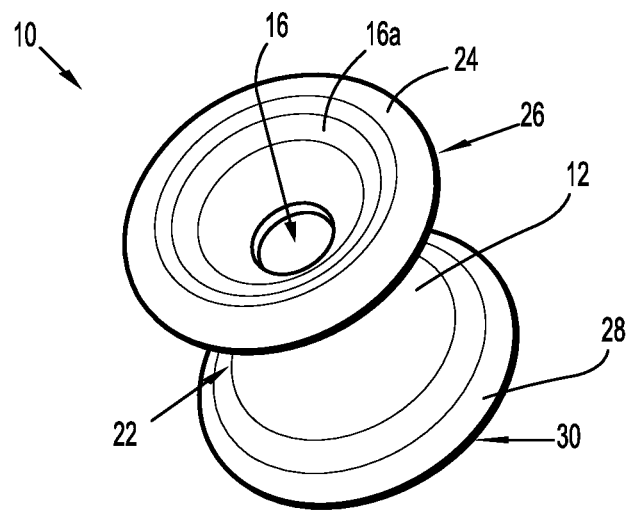
FIG. 1 is a front perspective view of the seal anchor apparatus.

In the drawings and in the description which follows, in which like references numerals identify similar or identical elements, the term "proximal" or "trailing" will refer to the end of the apparatus which is closest to the clinician during use, while the term "distal" or "leading" will refer to the end which is furthest from the clinician, as is traditional and known in the art.

Figure 2:
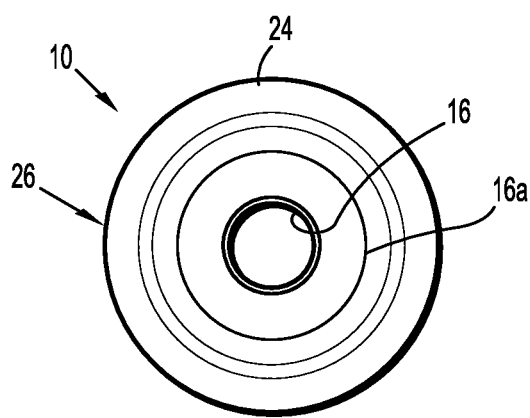
FIG. 2 is a top view of the seal anchor apparatus of FIG. 1.
Figure 3:
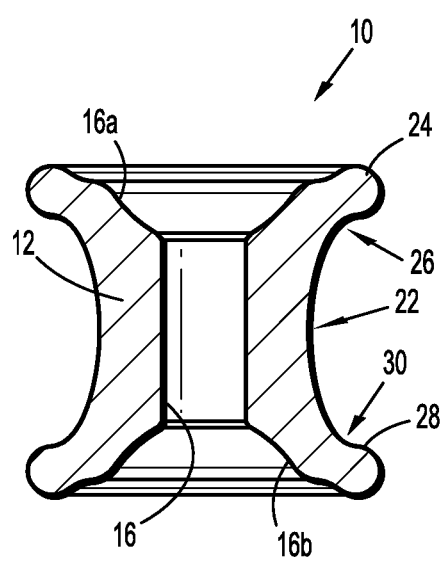
FIG. 3 is a longitudinal cross-sectional view of the seal anchor apparatus of FIG. 1.

Referring to FIGS. 1-3, there is disclosed a surgical seal anchor apparatus for use in single incision surgery. Surgical apparatus 10 is disclosed in commonly assigned U.S. patent application Ser. No. 12/578,832, filed Oct. 14, 2009 the entire contents of which disclosure are incorporated by reference herein. Surgical apparatus 10 is flexible or compressible to allow it to be inserted through a single incision in the body of a patient such that after insertion it will expand and seal within the incision. Additionally, the flexible nature of access assembly 10 allows a surgical instrument or object inserted therethrough to be manipulated about its axis and thus allow a higher degree of movement of the surgical instrument to orient it relative to the tissue being operated upon. Examples of surgical instruments or objects usable with surgical apparatus 10 include clip appliers, graspers, dissectors, retractors, staplers, laser probes, photographic devices, endoscopes and laparoscopes, tubes, and the like. Such instruments or objects will be collectively referred to herein as "objects".

Surgical apparatus 10 includes a flexible body or port 12 defining a single lumen 16. Proximal or trailing and distal or leading ends 16a, 16b, respectively, of lumen 16 may be tapered, as shown, to facilitate insertion of a surgical object therethrough. Port 12 may be formed of various materials such as, for example, silicone, thermoplastic elastomers (TPE), rubber, foam, gel, etc. In this manner, port 12 of access assembly 10 may be compressed or squeezed and inserted through an incision in the body of a patient. In one embodiment, port 12 includes TPE material that is infused with an inert gas, e.g. $CO_2$ or Nitrogen, to form a foam structure. Port 12 may be coated with a lubricant, e.g. Parylene N or C, in order to create a lubricious surface finish on all external surface. Various other coatings, e.g., hydrophilic, hydrophobic, bio-agents, anti-infection, analgesic, may also be employed to modify the properties of access assembly 10. In this manner, the coating facilitates insertion of port 12 into an incision and insertion of instruments therethrough.

Port 12 defines a substantially hourglass shape when viewed from the side, includes a central portion 22 having an upper rim or flange 24 located at a proximal end 26 of central portion 22 and a lower rim or flange 28 located at a distal end 30 of central portion 22. Upper rim 24 and lower rim 28 aid in minimizing movement of access assembly 10 longitudinally through an incision or tissue tract formed in a patient. Central portion 22 is of a length sufficient that upper rim 24 is maintained external the body while lower rim 28 is received within the abdominal cavity. As shown, upper and lower rims 24, 28, respectively, are substantially identical in size and shape. It is envisioned, however, that upper and lower rims 24, 28 may be of a different size and or shape.

Lumen 16 extends through port 12 and defines longitudinal axis configured to receive surgical instrument in a sealing manner. Lumen 16 may include a protective coating or sleeve (not shown), extending the length of port 12 to prevent tearing of access assembly 10 during insertion and removal of surgical instruments. The sleeve or coating may also facilitate insertion and removal of surgical instruments 50. The sleeves may be integrally formed with port 12, or instead may be securely affixed to port 12 using adhesive, ultrasonic welding or other suitable means.

Figure 4:
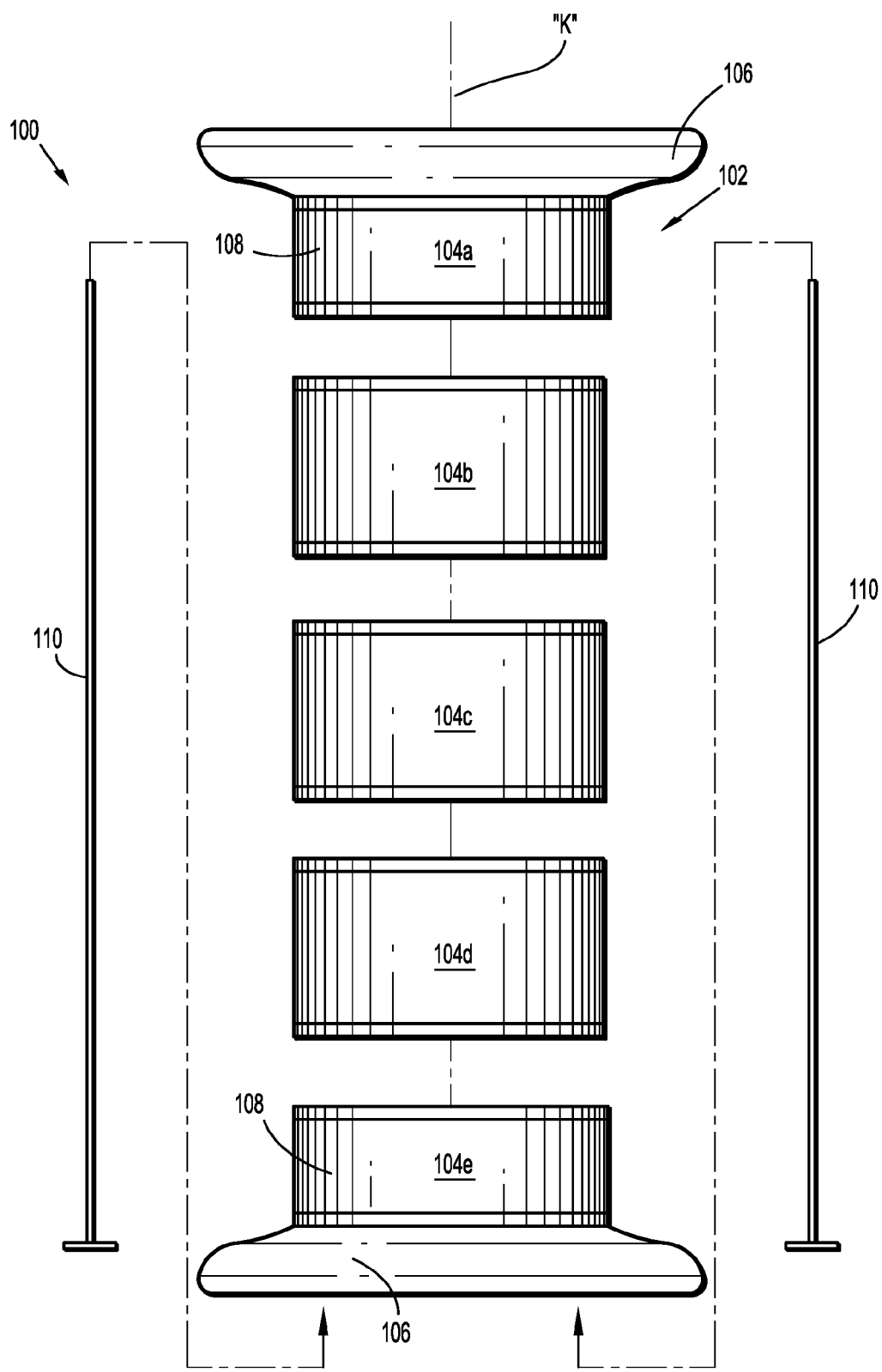
FIG. 4 is a plan view with parts separated of a seal anchor apparatus illustrating a plurality of anchor segments and a pair of securing elements for securing the anchor segments in adjacent stacked relation.

Referring now to FIG. 4, one embodiment of the seal anchor apparatus 100 of the present disclosure is illustrated. Seal anchor apparatus 100 includes seal anchor 102 having a plurality of anchor segments 104a-104e. Anchor segments 104a-104e are separable and are arranged to be positioned in adjacent stacked relation. The number of anchor segments 104a-104e utilized in a given procedure will be conditional upon the length of the tissue tract through which seal anchor 102 will be positioned. Moreover, the quantity of anchor segments 104a-104e utilized is selected in accordance with the length of the tissue tract. One or more anchor segments 104a-104e may be selected and utilized to perform the surgical procedure. Each anchor segment 104a-104e may be fabricated from any of the aforedescribed materials and be adapted to transition between compressed and expanded conditions for deployment within the tissue tract.

Anchor segments 104a, 104e are the trailing (or proximal) and leading (or distal) anchor segments, respectively. Each of anchor segments 104a, 104e may have an annular, peripheral or circumferential flange 106 at its respective trailing or leading ends and an anchor base 108. Flanges 106 define an enlarged cross-sectional dimension relative to anchor base 108 of anchor segments 104a, 104e. Flanges 106 assist in maintaining the seal anchor 102 within the tissue tract by engaging the external and internal surfaces of the tissue tract. Anchor bases 108 may be cylindrical in shape although other configurations are envisioned as well. Anchor bases 108 generally reside within the tissue tract when the seal anchor apparatus 100 is appropriated positioned within the tract.

Anchor segments 104b, 104c, 104d are the intermediate anchor segments and may define a cross-section substantially similar to the cross section of anchor base 108 of trailing and leading anchor segments 104a, 104e; however, it is possible that the cross-sections of anchor segments 104b, 104c, 104d may vary to correspond to the dimensioning of the tissue tract.

Seal anchor apparatus 100 also includes one or more elongated securing elements 110 which assist in maintaining anchor segments 104a-104e in adjacent stacked relation as will be discussed.

Figure 5:
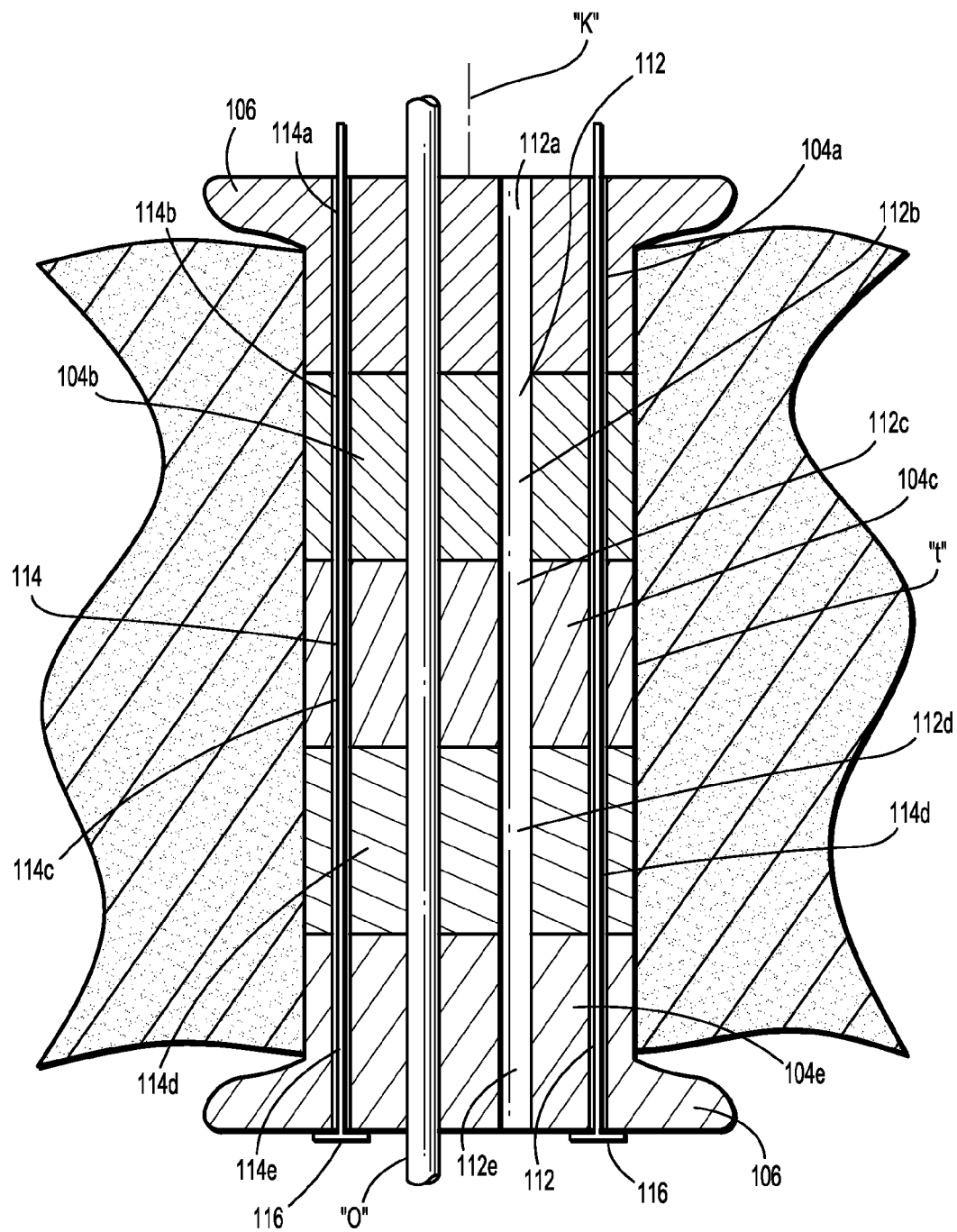
FIG. 5 is a longitudinal sectional view illustrating the anchor segments in the adjacent stacked relation with the securing elements and positioned within a tissue tract, and further illustrating a surgical object positioned within one of the object seal ports.

Referring now to the cross-sectional view of FIG. 5, in conjunction with FIG. 4, when assembled in adjacent stacked relation, anchor segments 104a-104e define at least one longitudinal object port 112 extending through seal anchor 102 and relative to the longitudinal axis "k" of the seal anchor 102. Object port 112 is adapted to receive a surgical object in substantial sealed relation therewith, i.e., the internal surfaces defining the object port 112 engage the object and establish a substantial seal about the outer surfaces of the object. In particular, each anchor segment 104a-104e defines a respective object port segment 112a-112e extending through the anchor segment 104a-104e. When anchor segments 104a-104e are appropriately arranged in the adjacent stacked relation, port segments 112a-112e may be aligned to define one continuous object port extending through seal anchor 102. In FIG. 5, two object ports 112 are shown having respective port segments 112a-112e in longitudinal alignment.

Seal anchor 102 further defines one or two supplemental longitudinal openings 114 extending the longitudinal length of the seal anchor 102. For example, each anchor segment 104a-104e may include supplemental opening segments 114a-114e extending through the respective anchor segments 104a-104e, which, when the anchor segments 104a-104e are appropriately assembled, the supplemental opening segments 114a-114e are aligned to define the continuous supplemental longitudinal openings 114. Two supplemental longitudinal openings 114 are depicted in FIG. 5.

Figure 6:
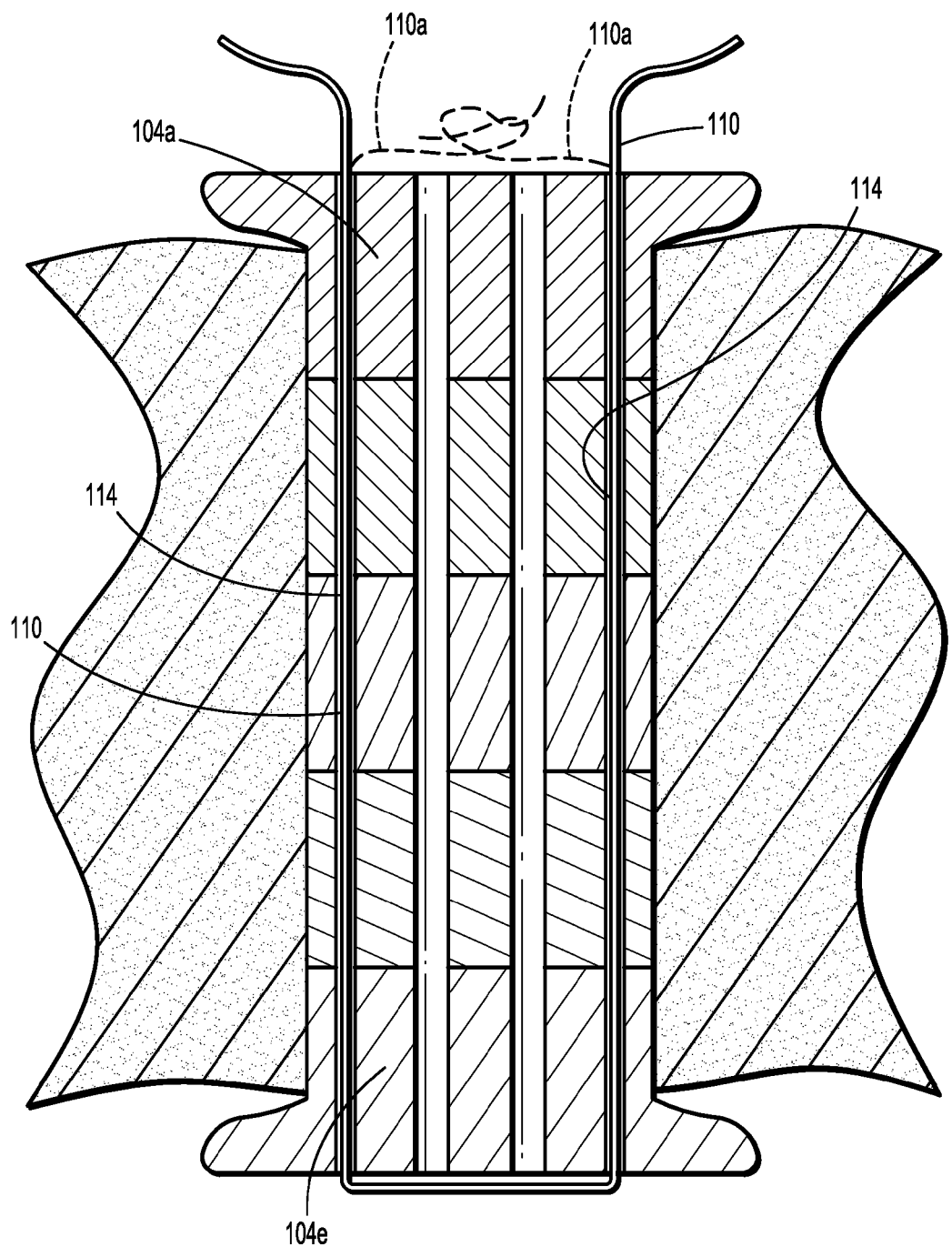
FIG. 6 is a sectional view similar to the view of FIG. 5 illustrating an alternate securing element for securing the anchor segments.

Supplemental longitudinal openings 114 are dimensioned to receive one or more elongated securing elements 110 which function in securing or retaining the anchor segments 104a-104e in the adjacent stacked relation. Securing elements 110 extend through supplemental opening segments 114a-114e of each anchor segment 104a-104e. In one embodiment depicted in FIG. 5, securing elements 110 may be relatively rigid and have lips 116 adjacent its leading end with a cross-section greater than the cross-section of a supplemental longitudinal opening 114 to engage the leading anchor segment 114e. In another embodiment depicted in FIG. 6, the securing element is a single flexible filament which is passed though longitudinal supplemental openings 114 whereby the free ends of the filament extend in a proximal or trailing direction from trailing anchor segment 104a. The free ends 110a may be tied (shown in phantom) to secure the anchor segments 104a-104e to each other.

Referring again to FIG. 5, seal anchor member 102 is shown positioned within a tissue tract "t". Flanges 106 and trailing and leading anchor segments 106a, 106b are shown engaging the external and internal surfaces adjacent the tissue tract "t". An object "o" is positioned within one longitudinal object port 112.

The use of access assembly 10 in a single incision surgical procedure will now be described. A tissue tract "t" is established through body tissue to access an underlying tissue site. The tissue tract "t" may be performed with a trocar, scalpel or the like, or may be a natural body orifice or channel. The length of the tissue tract is approximated by the clinician. Thereafter, anchor segments 104a-104e are assembled with one or more of the leading and trailing anchor segments 104a, 104e and one or more of the intermediate anchor segments 104b-104d arranged in adjacent stacked relation. The number of anchor segments 104a-104e utilized generally will correspond to the length of the tissue tract, and this will be decided by the clinician. The longitudinal object port segments 112a-112e and supplemental opening segments 114a-114e of the anchor segments 102a-102e are longitudinally aligned. One or more securing members 110 are positioned within the supplemental longitudinal openings 114 to secure the anchor segments 104a-104e to each other.

The seal anchor 102 is advanced within the tissue tract "t". During insertion, the individual anchor segments 104a-104e may be compressed to permit advancement through the tissue tract. Once appropriately positioned within the tissue tract, the anchor segments 104a-104e will attempt to return to their inherent expanded condition which, thereby effects a seal of the outer surfaces of the anchor segments 104a-104e relative to the tissue tract "t". One or more surgical instruments or objects "o" are introduced through object ports 112 of the seal anchor 102 to perform one or more surgical tasks. Object ports 112 establish a substantial sealed relation with the surgical objects as discussed.

Figure 7:
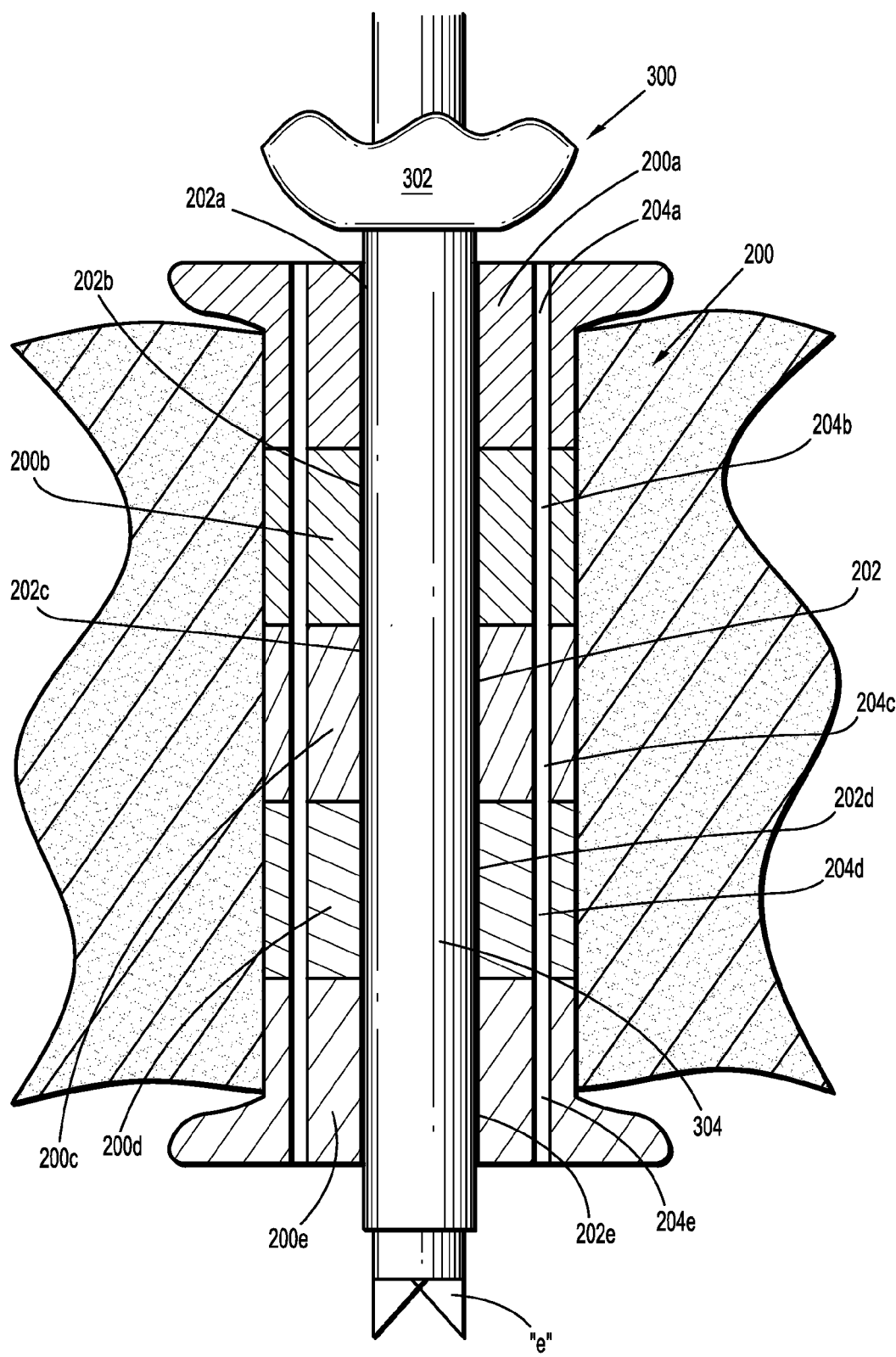
FIG. 7 is a longitudinal sectional view similar to the view of FIG. 6 illustrating an alternate embodiment of the seal anchor apparatus with a surgical trocar positioned within the apparatus.

FIG. 7 illustrates an alternate embodiment where seal anchor member 200 includes a centrally positioned object port 202 in general alignment with the central longitudinal axis "k" of seal anchor member 200. Seal anchor member 200 includes a plurality of anchor segments 200a-200e having object port segments 202a-202e and supplemental opening segments 204a-204e. Object port segments 202a-202e and supplemental opening segments 204a-204e are aligned when the anchor segments 202a-202e are in stacked relation to define one or more longitudinal object ports 202 for passage of a surgical object and one or more supplemental opening 204 for reception of a securing member as discussed in connection with the earlier embodiments.

A cannula 300 may be introduced within object port 202. One suitable cannula 300 is disclosed in commonly assigned U.S. Patent Publication No 20060224120 to Smith et al., the entire contents of which disclosure are hereby incorporated by reference herein. Cannula 300 includes cannula housing 302 and cannula sleeve 304 extending from the cannula housing 302. An instrument seal may be disposed within the cannula housing 302 to establish a substantial sealed relation about an instrument inserted therethrough. One suitable instrument seal is disclosed in commonly assigned U.S. Pat. No. 7,244,244 to Racenet, the entire contents of which disclosure are hereby incorporated by reference herein. The seal member disclosed in the Racent '244 patent may comprise a resilient center material (e.g., polyisoprene or natural rubber) with first and second layers of fabric at the respective proximal and distal surfaces of the resilient material and impregnated with the resilient material. The fabric may be of any suitable fabric for example, a SPANDEX material containing about 20% LYCRA and about 80% NYLON available from Milliken, In FIG. 7, a surgical instrument or object "o" is shown introduced within cannula 300 and has an end effector "e" for performing a surgical task.

Although the illustrative embodiments of the present disclosure have been described herein with reference to the accompanying drawings, the above description, disclosure, and figures should not be construed as limiting, but merely as exemplifications of particular embodiments. It is to be understood, therefore, that the disclosure is not limited to those precise embodiments, and that various other changes and modifications may be effected therein by one skilled in the art without departing from the scope or spirit of the disclosure.

What is claimed is:

1. A surgical apparatus for positioning within a tissue tract accessing an underlying body cavity, comprising:
   a seal anchor member transitionable between an expanded condition and a compressed condition, the seal anchor member including a distal end, a proximal end, a longitudinal length defined between the proximal and distal ends, and a plurality of anchor segments selectively arranged in superposed relation along a longitudinal axis defined by the seal anchor member, each anchor segment defining an object port segment and a supplemental port segment spaced apart from the object port segment, the object port segments being aligned to define a longitudinal object port configured to receive a surgical object therethrough, the supplemental port segments being aligned to define a longitudinal supplemental port dimensioned to receive a securing member configured to retain the plurality of anchor segments in the superposed relation along the longitudinal axis of the seal anchor member, wherein the object port segment of a proximal-most anchor segment of the plurality of anchor segments is obstructed from the supplemental port segment of the proximal-most anchor segment such that the longitudinal object port and the longitudinal supplemental port are completely closed off from one another along the entire length of the seal anchor member.

2. The surgical apparatus according to claim 1, wherein the longitudinal object port is configured to receive the surgical object in a sealing relation.

3. The surgical apparatus according to claim 1, wherein the seal anchor member comprises one of a foam material or a gel material.

4. The surgical apparatus according to claim 1, wherein the securing member is coupled to the distal end of the seal anchor member.

5. The surgical apparatus according to claim 4, wherein the securing member includes a flexible filament.

6. The surgical apparatus according to claim 4, wherein the securing member includes a rigid element.

7. The surgical apparatus according to claim 1, wherein the seal anchor member includes at least three anchor segments.

8. The surgical apparatus according to claim 1, wherein the plurality of anchor segments include a leading anchor segment, a trailing anchor segment, and an intermediate anchor segment, at least one of the leading or the trailing anchor segments having a flange portion.

9. The surgical apparatus according to claim 8, wherein the leading and the trailing anchor segments each include a flange portion.

10. The surgical apparatus according to claim 1, wherein the seal anchor member further defines a plurality of longitudinal object ports.

11. A surgical apparatus for positioning within a tissue tract accessing an underlying body cavity, comprising:
a seal anchor member transitionable between an expanded condition and a compressed condition, the seal anchor member including a distal end, a proximal end, a longitudinal length defined between the proximal and distal ends, a plurality of anchor segments arranged in superposed relation along a longitudinal axis defined by the seal anchor member, each anchor segment selectively removable, the seal anchor member defining a longitudinal object port configured to receive a surgical object therethrough, and a longitudinal channel dimensioned to receive a securing member configured to retain the plurality of anchor segments in the superposed relation along the longitudinal axis of the seal anchor member, wherein a proximal-most portion of the longitudinal channel is obstructed from a proximal-most portion of the longitudinal object port when the plurality of anchor segments are arranged in the superposed relation along the longitudinal axis of the seal anchor member such that the longitudinal object port and the longitudinal channel are completely closed off from one another along the entire length of the seal anchor member.

12. The surgical apparatus according to claim 11, wherein each anchor segment defines a port segment, the port segments of the plurality of anchor segments being aligned to define the longitudinal object port extending between distal and proximal ends of the seal anchor member.

13. The surgical apparatus according to claim 11, wherein the securing member is coupled to a distal end of the seal anchor member.

14. The surgical apparatus according to claim 11, wherein the plurality of anchor segments include a leading anchor segment, a trailing anchor segment, and an intermediate anchor segment, at least one of the leading or the trailing anchor segments having a flange portion.

15. The surgical apparatus according to claim 14, wherein the leading and the trailing anchor segments each include a flange portion.

16. The surgical apparatus according to claim 11, wherein the longitudinal object port extends along the entire length of the seal anchor member.

* * * * *